(12) United States Patent
Arnold et al.

(10) Patent No.: US 7,788,965 B2
(45) Date of Patent: Sep. 7, 2010

(54) PORTABLE FRICTION TESTING DEVICE

(75) Inventors: William Allen Arnold, Akron, OH (US); Chenghsiung Lin, Hudson, OH (US); Christopher Aldrich Brown, Cazenovia, NY (US); Torbjorn Stansen Bergstrom, Worcester, MA (US); Douglas Jeffrey Geiger, Basseterre (KN)

(73) Assignee: The Goodyear Tire + Rubber Company, Inc., Akron, OH (US)

( * ) Notice: Subject to any disclaimer, the term of this patent is extended or adjusted under 35 U.S.C. 154(b) by 188 days.

(21) Appl. No.: 11/931,579

(22) Filed: Oct. 31, 2007

(65) Prior Publication Data

US 2009/0107210 A1   Apr. 30, 2009

(51) Int. Cl.
*G01N 19/02*   (2006.01)
(52) U.S. Cl. .......................................................... 73/9
(58) Field of Classification Search ................. 73/9
See application file for complete search history.

(56) References Cited

U.S. PATENT DOCUMENTS

| | | | | |
|---|---|---|---|---|
| 1,668,593 A * | 5/1928 | Jones | ............................... | 73/9 |
| 2,225,140 A * | 12/1940 | Walker | ............................ | 73/9 |
| 3,161,704 A * | 12/1964 | Le Grand et al. | ........... | 264/40.1 |
| 3,538,742 A * | 11/1970 | Benning | ......................... | 73/9 |
| 3,977,231 A * | 8/1976 | Haehner et al. | ................... | 73/9 |
| 4,026,141 A * | 5/1977 | Merritt | ............................. | 73/9 |
| 4,051,713 A * | 10/1977 | Bao et al. | ........................ | 73/9 |
| 4,173,885 A | 11/1979 | Matlock | | |
| 4,187,714 A * | 2/1980 | Cox et al. | ......................... | 73/9 |
| 4,524,602 A * | 6/1985 | Moore | ................................ | 73/9 |
| 4,536,995 A * | 8/1985 | Frederick | ....................... | 52/27 |
| 4,813,266 A * | 3/1989 | Nash | ................................. | 73/9 |
| 4,895,015 A * | 1/1990 | English | ........................... | 73/9 |
| 4,909,073 A * | 3/1990 | Takahashi et al. | .............. | 73/146 |
| 5,113,688 A * | 5/1992 | Lazeration | ....................... | 73/8 |
| 5,216,608 A | 6/1993 | Ito et al. | | |
| 5,245,856 A * | 9/1993 | Pazzaglia et al. | ................. | 73/9 |
| 5,736,630 A * | 4/1998 | Welner | ............................ | 73/9 |
| 6,108,497 A * | 8/2000 | Nakayama et al. | .......... | 396/429 |
| 6,430,520 B1 * | 8/2002 | Tranquilla | .................... | 702/141 |
| 7,509,847 B2 * | 3/2009 | Halliday | ...................... | 73/146 |
| 2006/0162420 A1 * | 7/2006 | Pappas et al. | ..................... | 73/9 |

FOREIGN PATENT DOCUMENTS

GB   2419962 A   *   5/2006

* cited by examiner

*Primary Examiner*—David A. Rogers
(74) *Attorney, Agent, or Firm*—Roger D. Emerson; Timothy D. Bennett; Emerson, Thomson Bennett (57) ABSTRACT

A portable device for measuring friction, especially friction between tire treads and road surfaces is disclosed. The portable friction tester is shaped as an equilateral triangle providing three points of contact for samples in the road surface.

20 Claims, 6 Drawing Sheets

PORTABLE FRICTION TESTING DEVICE

I. BACKGROUND OF THE INVENTION

A. Field of Invention

This invention pertains to the art of methods and apparatuses for measuring friction between two surfaces, and more specifically, methods and apparatuses for measuring the friction between rubber compounds as used for tires and similar materials and road surfaces; these measurements can be used to understand the friction between tires and road surfaces.

B. Description of the Related Art

It is known in the art for the measurement of friction between various surfaces, and it is also known to measure the frictional forces generated by tires, such as automobile, truck, aircraft tires, on various road surfaces. It is also known to attempt to measure these frictional forces accurately through means of testing devices.

U.S. Pat. No. 4,187,714 to Cox, et al. purportedly shows a portable surface friction tester for use in an automobile tire/road surface application.

U.S. Pat. No. 4,173,885 to Matlock illustrates another standard surface assembly that can be purportedly be used to measure friction between a rubber tire and a surface.

U.S. Pat. No. 5,216,608 to Ito, et al. purportedly discloses an apparatus and method for estimating the friction coefficient of a road surface and a vehicle.

The present invention provides methods and apparatuses for an innovative apparatus and method for measuring frictional forces between two surfaces, and more specifically frictional forces between rubber compounds as used for tires and similar materials and a road surface.

II. SUMMARY OF THE INVENTION

According to one aspect of the present invention, a new and improved method and apparatus for measuring for measuring friction between rubber compounds as used for tires and similar materials and a road surface is provided. The friction measuring device provides advantages, both in utility and ease of use, over previous designs.

One advantage of this invention is the fact that the unit tends to maintain constant force of all samples on the road surface. Another advantage is the fact that the triangular configuration ensures the desired contacts, as a plane is defined by three points.

Another advantage of the invention is the fact that the pressure can be adjusted by adding weights to the device, or, the size of the sample can be increased or decreased to effect any desired changes in pressure.

Another advantage of the invention is its portability. With the inventive device, it is not necessary to cut out samples and take them back to the lab, or to drive entire vehicles and tires over actual pavement, to obtain meaningful data. Rather, accurate and meaningful data can be obtained inexpensively, from actual road surfaces and actual road conditions, by translating the disclosed device across the road surface to be measured.

Yet another advantage of this invention is the possible adjustability. The inventive device can be adjusted for speed and distance traveled. The pressure can also be adjusted by changing the point of contact.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION OF THE INVENTION

Figure 1:
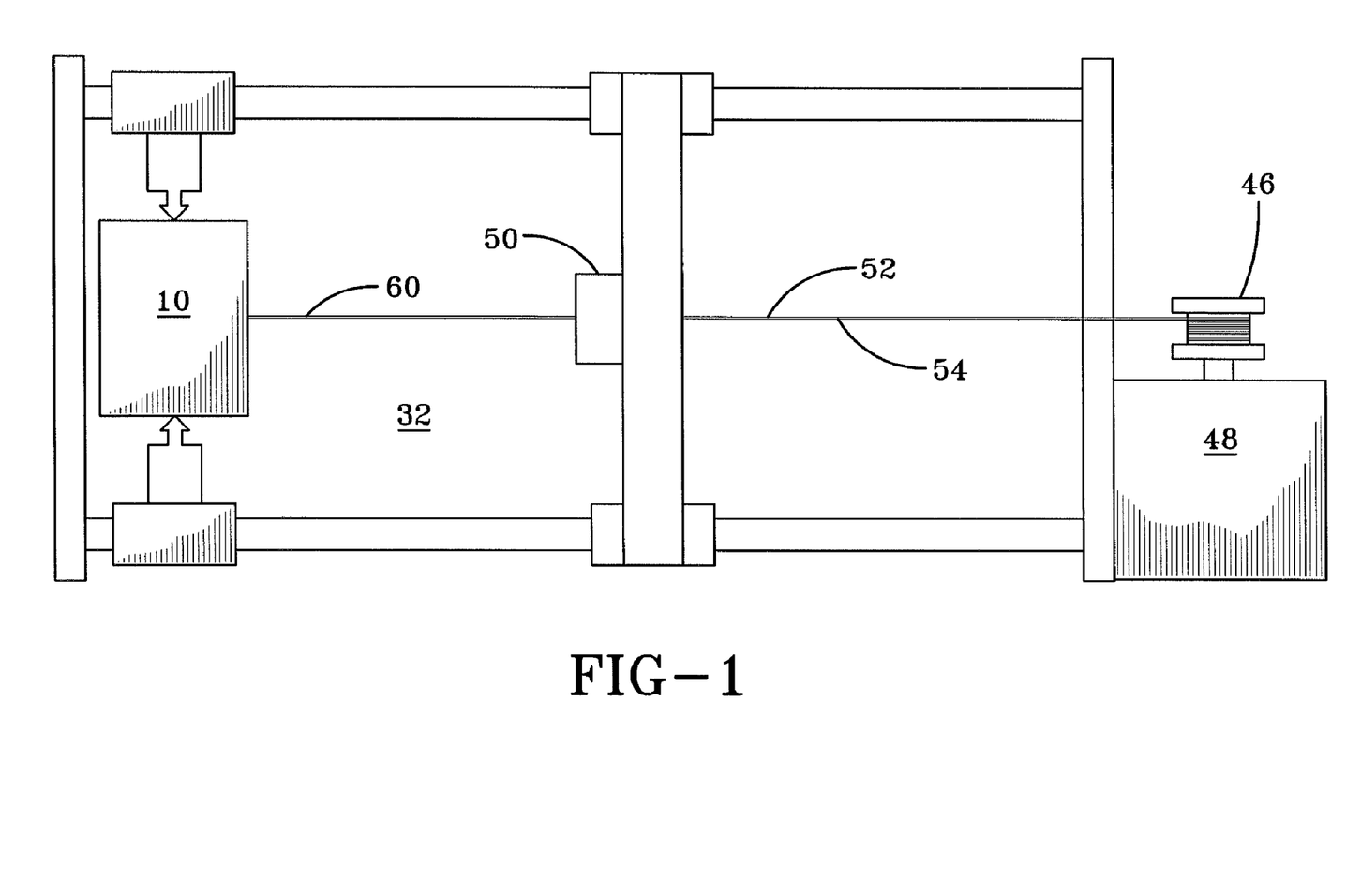
FIG. 1 is a top view of a device according to the invention, showing its environment in one manner of operating the device according to the invention.

Referring now to the drawings wherein the showings are for purposes of illustrating embodiments of the invention only and not for purposes of limiting the same, FIG. 1 shows a top or overhead view, schematically of one manner of carrying out the inventive method using the inventive device.

Figure 2:
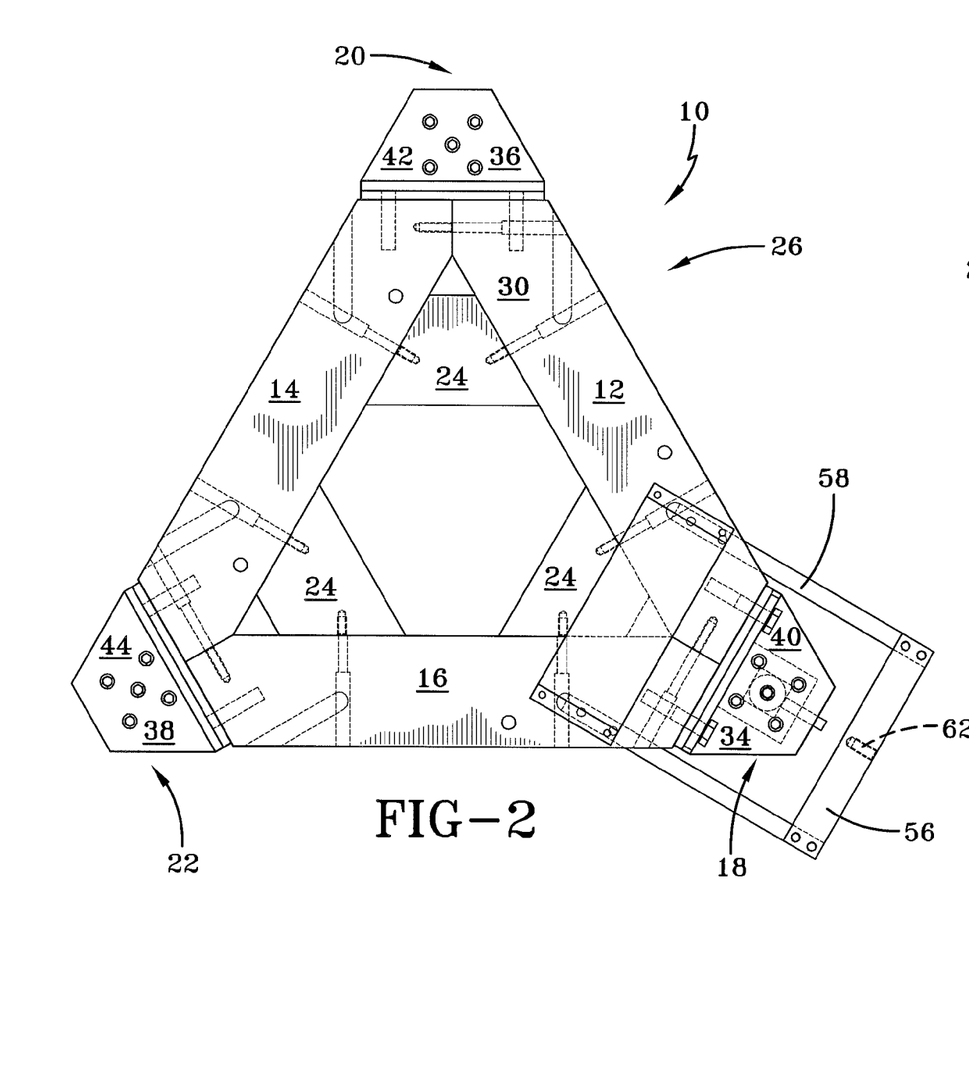
FIG. 2 is a top view of the device.
Figure 3:
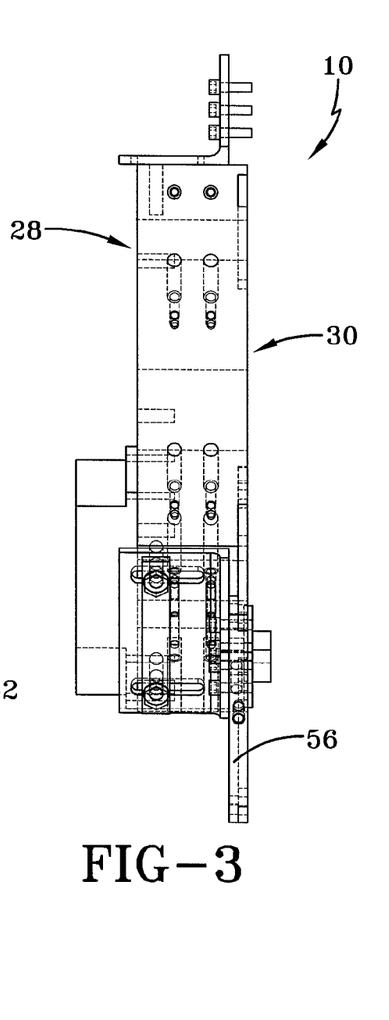
FIG. 3 is a side view of the device.
Figure 4:
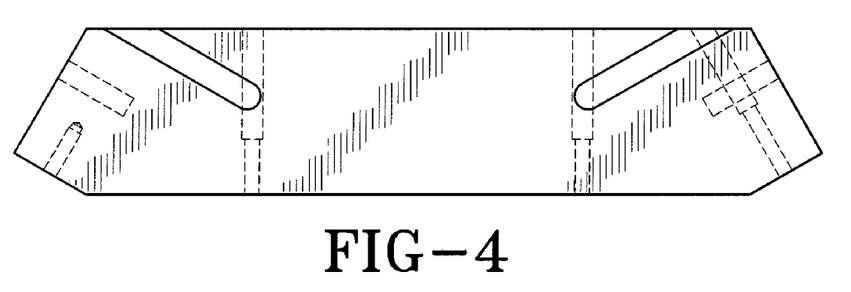
FIGS. 4-17 are drawings of individual components of the assembly shown in FIGS. 1-3.
Figure 5:
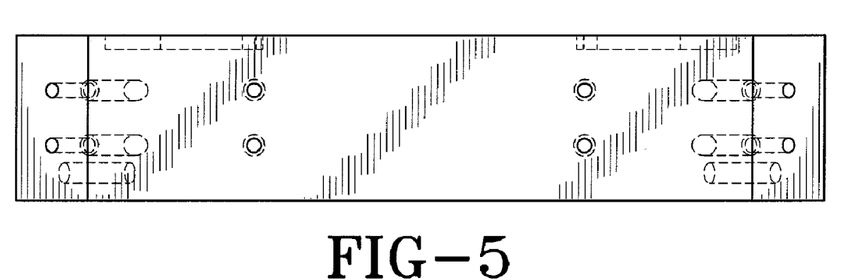
Figure 6:
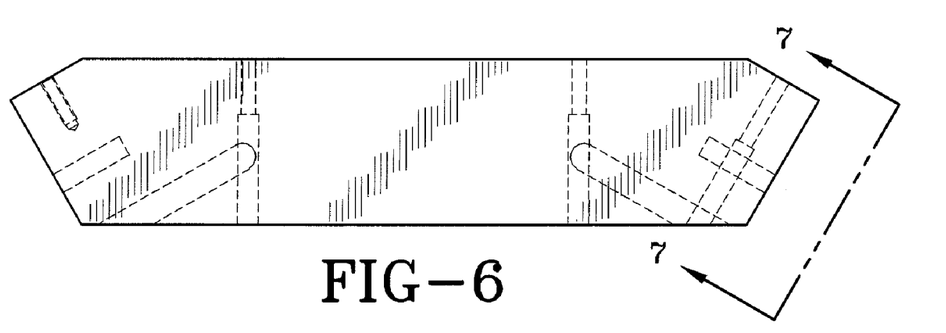
Figure 7:
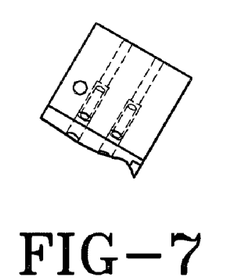
Figure 8:
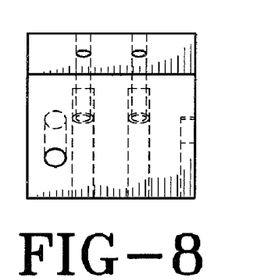
Figure 9:
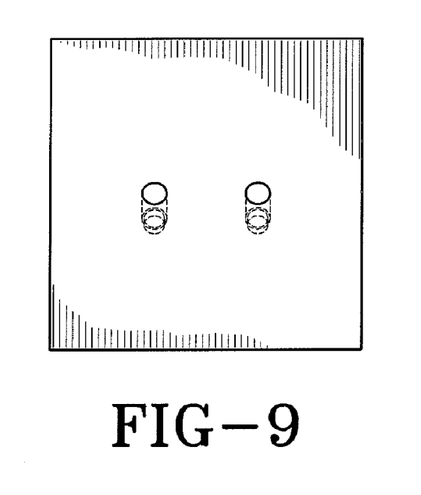
Figure 10:
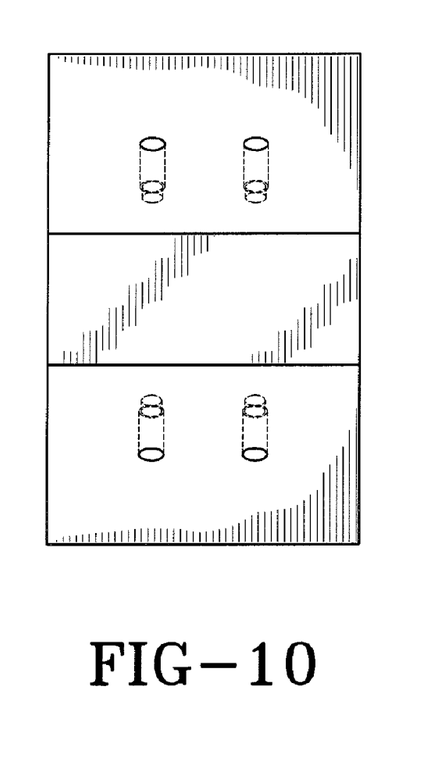
Figure 11:
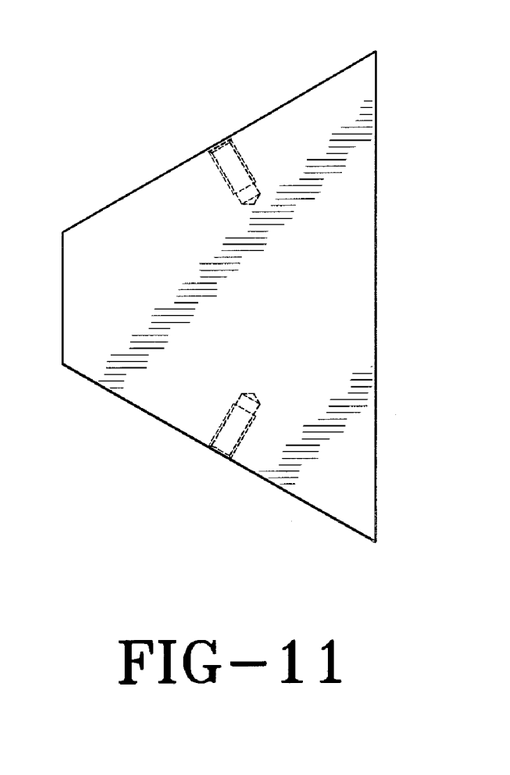
Figure 12:
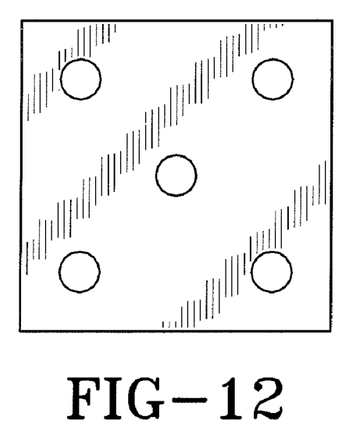
Figure 13:
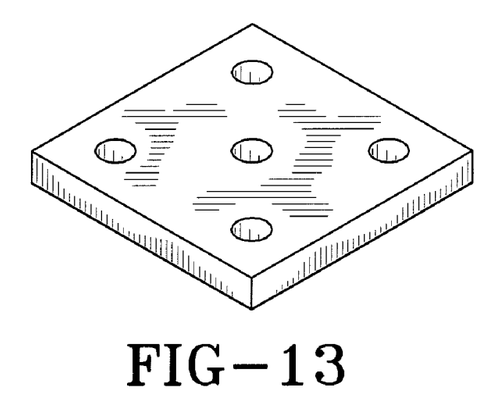
Figure 14:
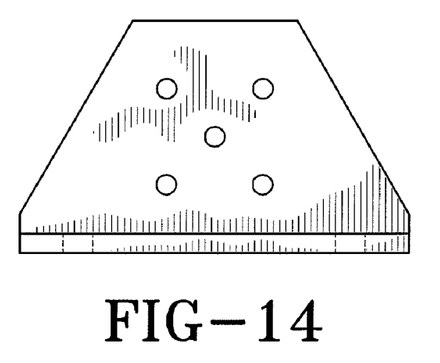
Figure 15:
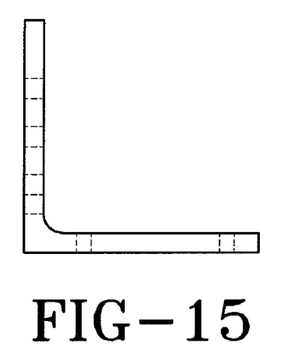
Figure 16:
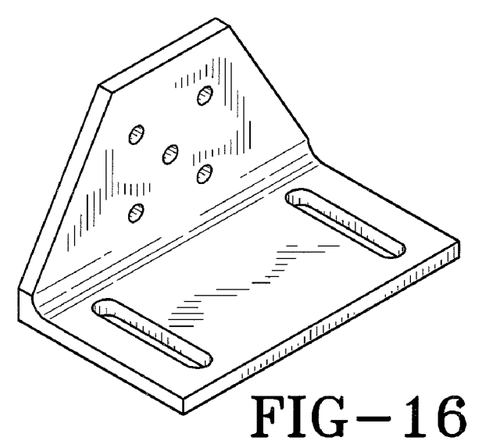
Figure 17:
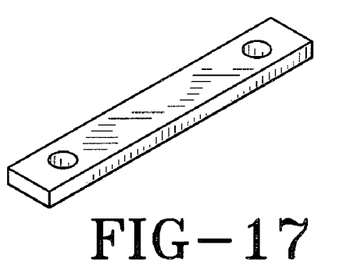

With reference now to FIGS. 1-3, the inventive device 10 is configured generally in the shape of an equilateral triangle. The equilateral triangle comprises first leg 12, second leg 14, and third leg 16. These legs, being of approximately identical length, comprise three equal legs of an equilateral triangle, and thereby form points, specifically first point 18, second point 20, and third point 22. A first, second, and third legs 12, 14, 16 are braced by members 24 which together comprise a frame 26. The frame 26 may be formed to have any stiffness property chosen with sound engineering judgment. In one embodiment, the frame 26 is relatively stiff—the members 24 add weight and stiffness. The triangular shape may act as a truss also providing additional stiffness.

With continuing reference to FIGS. 1-3, the device has an upper side 28 and an underside 30. The underside 30 of the device 10 is the side that faces the associated road surface 32.

With continuing reference to FIGS. 1-3, the device 10 has a first contacting region 34 located at the first point 18. Similarly, the device 10 has a second contacting region 36 at the second point 20 and a third contacting region 38 at the third point 22. The contacting regions are the regions of the device 10 which generally come in contact with the surface whose frictional interface is to be measured. For example, in one primary application of the inventive device 10, an associated pavement or road surface 32 is to be measured, and the friction between that associated road surface 32 and various associated tire material samples is to be measured. The triangular shape, and specifically the equilateral triangular shape of the device 10, helps ensure that the samples (not shown) remain in proper contact with the associated road surface 32. Since three points are necessary to define a plane, the three points of this portable device 10 for testing friction are ideal to maintain constant contact with the road surface.

Still referring to FIGS. 1-3, on the underside 30 of the device 10, a first sample holder 40 is located at the first contacting region 34. Similarly, a second sample holder 42 is located at the second contacting region 36 and a third sample holder 44 is located at the third contacting region 38. The sample holders 40, 42, 44, may use any sample holding mechanism chosen with sound engineering judgment. The sample holders can be fitted with the sample desiring to be studied. In the primary application of this invention, portions of tire material (not shown) are mounted into the sample holders 40, 42, 44 so that the device 10 may be translated at a constant or precisely measured speed. The device is preferably made of brass and therefore has a substantial weight already, but can be further weighted with weights to create the sort of conditions desired. In addition, if desired, road surface conditions, such as oil-soaked, rain on top of an oil film, snow, ice, etc. may be simulated by adding those materials to the road surface, or pulling the device across a road surface having those conditions. In addition, the size of the samples (not shown) mounted in the first, second, and third sample holders may vary, and thereby the amount of pressure or stress seen at the interface of the first frictional surface (often the road surface) and the second frictional surface (the surface of the sample to be measured) may be controlled.

With continuing reference to FIGS. 1-3, in one embodiment of the invention, the translational force is supplied by a winch 46 driven by a motor 48. In one embodiment, the speed at which the winch 46 draws the device 10 across the associated first frictional surface 32 is controllable. In addition, a measurement device, such as a force transducer 50 may be mounted between the device 10 and a tensile-carrying member 52. The tensile-carrying member 52 is most preferably a rope, or a cable, or a rod, or some other sort of inextensible member which can provide accurate information through the transducer 50. However, in an alternate embodiment, a tensile-carrying member can be replaced with a compression carrying member 54 in the event that the operator of the test believes more important data may be obtained by pushing device 10 rather than pulling it.

With reference to FIGS. 1-3, a translational connection 56 is located at a first point 18 of the device 10. While the form of the translational connection may vary, it is essentially a way to connect the device 10 to the tensile-carrying member 52 in a way that does not detrimentally impact the acquisition of data. In one embodiment, the translational connection 56 is a U-Shaped bracket 58 which can be secured to the device 10. The translational connection 56 may be attached to the bottom of the device 10 so that the pulling point is relatively low. In one embodiment, the translational connection 56 is attached to the device 10 as close to the level of the frictional force as possible. In this way, forces that create moments that would tend to rotate the device 10 onto the sample are nearly eliminated. Similarly, a second tensile-carrying member 60 may be attached, such as through tapped hole 62 to the U-Shaped bracket 58.

With reference now to FIGS. 4-17, various components of the device are illustrated separately and disassembled, while in FIGS. 1-3 those same components are shown in an assembled view.

Figure 18:
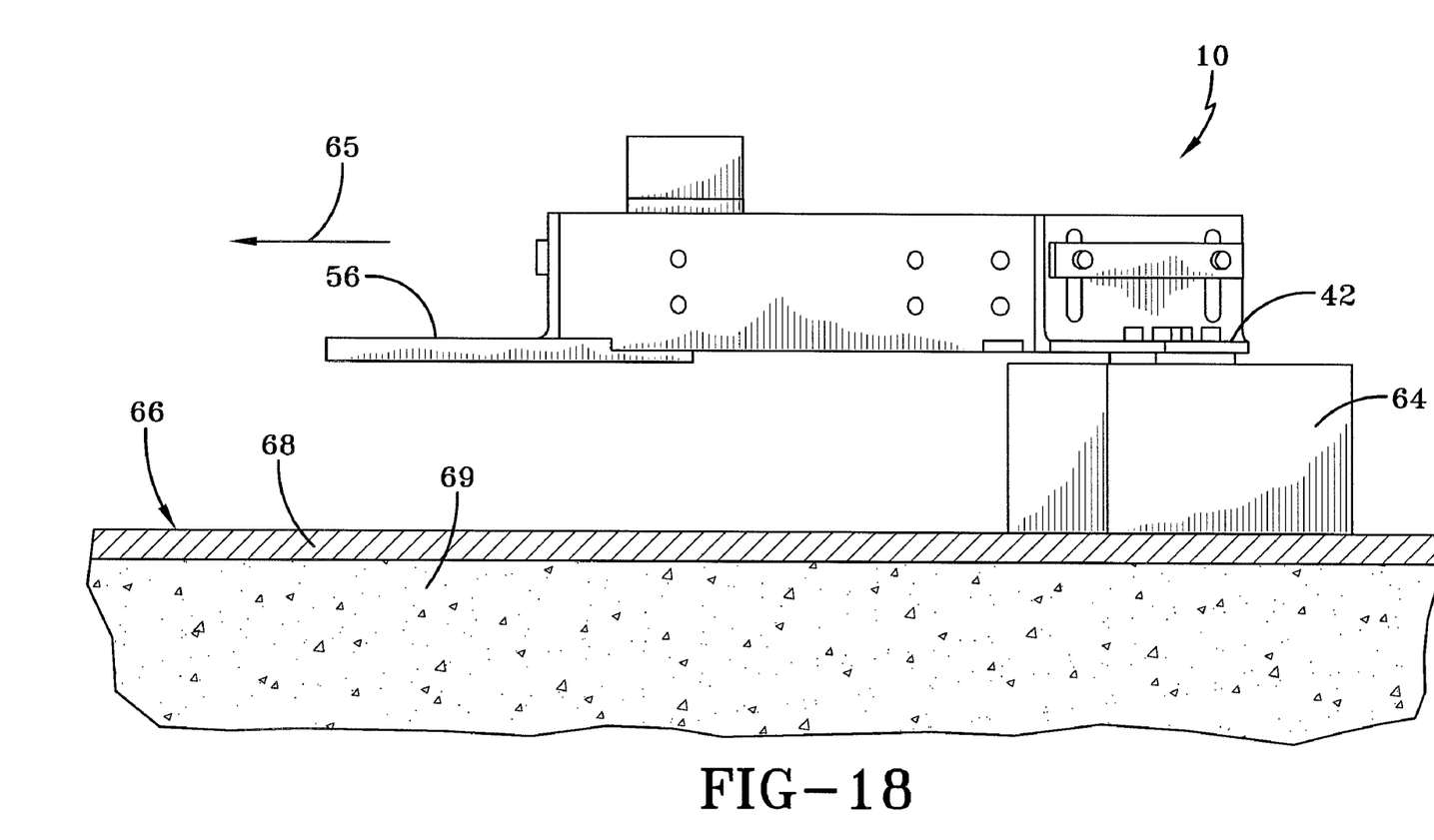
FIG. 18 is a side, cross-sectional schematic view of an associated sample being translated across an associated road surface, thereby to obtain a coefficient of frictional force between the two surfaces.

With reference now to FIG. 18, a schematic, side view of the device, the sample holders 40, 42, 44, and an associated sample 64 is illustrated. The sample 64 is mounted to a sample holder 42. Other samples (not shown) of similar type and variety are mounted in the first sample holder 40 and the third sample holder 44, but are not shown here for clarity. The sample(s) may have any shape and any size chosen with sound engineering judgment. The sample 64 shown, for example, has a thickness. It is to be understood that this thickness can vary as desired. In one specific embodiment, for example, the thickness of the sample 64 is much smaller than shown so that the device 10 is positioned closer to the road surface 66. The device 10 is translated in the direction of arrow 65 by the translational connection 56 being acted upon by either tensile-carrying member 52 or compression-carrying member 54, as the case may be. In one embodiment, the tensile-carrying member 52 pulls on translational connection 56 in the direction of arrow 65, causing there to be relative motion between the sample 64 and the associated road surface 66. Here, the road surface is shown in a cross-sectional view, having a first layer 68 and a second layer 69. One of the primary advantages of the subject invention is that each road surface 66 is different, as it is comprised of different layers, 68, 69, which could react differently to weather conditions (not shown) and the like, resulting in different frictional properties, changing with speed and pressure and the materials. Prior to the present invention, the only relevant, accurate data that could be obtained required actual driving of a vehicle over road surface 66, at considerable cost and inconvenience, due to the development and invention of the current device 10, accurate information about frictional forces generated by the movement of sample 64 across road surface 66 at controlled and measured speeds generated by motor 48 and winch 46 as measured by transducer 50 can now be obtained. In one embodiment, sample 64 comprises portions of tire materials or of tires. The tire samples can be aligned within the first, second, and third sample holders 40, 42, 44 so that the treads are facing in the same direction and are aligned, thereby duplicating and recreating the effect of a tire footprint on the road surface.

With reference now to FIGS. 1-3 and 18, in one embodiment, the device 10 is pulled from any one of the contacting regions (the first contacting region 34, for example, acting as the front contacting region) with the other two contacting regions (the second and third contacting regions 36 and 38, for example, acting as the back contacting regions) trailing behind. With this arrangement, the device 10 self aligns as it is pulled—more resistance occurs in the back, like feathers on an arrow—reducing any tendency for the device 10 to rotate about a vertical axis. In another embodiment, the back contacting regions were fitted with low friction material and operated on a low friction surface. With this arrangement, only the front contacting region was tested. In yet another embodiment, the back contacting regions can be moved forward or backward in order to adjust the force exerted on the front contacting region.

With continuing reference to FIGS. 1-3 and 18, in one embodiment, the heights of one or more of the contacting regions 34, 36, 38 are adjustable so that the device 10 can be positioned as close to the pavement as desired. The height may be adjusted with the use of shims. After mounting the sample(s) 64, the shims may be placed under the sides of the frame 26. The brackets are loosened so that it sits on the shims, then the brackets are tightened and the shims removed. The shims provide a means of assuring that the device is close to the pavement. In yet another embodiment, the translational connection 56 is designed so that the pull force vector on the device 10 can be positioned as close as possible to co-linear (same horizontal plane) as the sum of the friction force vectors on the sample(s).

The embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

Having thus described the invention, it is now claimed:

1. A device for measuring friction, the device comprising:
   a frame, the frame having first, second and third contacting regions, the first, second and third contacting regions capable of contacting an associated first frictional surface; and,
   a first sample holder, the first sample holder located near the first contact region, the first sample holder capable of securing an associated first sample in a position to contact the associated first frictional surface, wherein the height of the first sample holder is adjustable.

2. The device of claim 1 wherein pressure seen by the associated sample is adjustable by varying the size of the sample.

3. The device of claim 1 wherein the frame stiffness is adjustable.

4. The device of claim 1 further comprising:
   a second sample holder, the second sample holder located near the second contact region, the second sample holder capable of securing an associated second sample in a position to contact the associated first frictional surface, wherein the height of the second sample holder is independently adjustable from the first sample holder; and
   a third sample holder, the third sample holder located near the third contact region, the third sample holder capable of securing an associated third sample in a position to contact the associated first frictional surface, wherein the height of the third sample holder is independently adjustable from the first and second sample holders.

5. The device of claim 1 wherein the frame is generally triangular chosen from the group comprising right triangles, acute triangles, obtuse triangles, isosceles triangles, scalene triangles, and equilateral triangles.

6. The device of claim 5 wherein the frame further comprises at least one brace member operatively attached to two sides of the generally triangular frame to increase the stiffness of the frame.

7. The device of claim 1 further comprising:
   a translational connection, the translational connection being located a first point of the frame of the device.

8. The device of claim 7 wherein the translational connection is located at substantially the same height as a friction force generated by a translation of the device.

9. The device of claim 1 the first contacting region is on an underside of a first point of the frame.

10. The device of claim 9 wherein the second contacting region is on an underside of a second point of the frame and the third contacting region is on an underside of a third point of the frame.

11. The device of claim 1 further comprising:
    a movement generator, the movement generator selectively translating the device relative to the associated first frictional surface.

12. The device of claim 11 wherein the movement generator comprises:
    a compression-carrying member, the compression-carrying member being selectively attached to the translational connection.

13. The device of claim 11 wherein the movement generator comprises:
    a tensile carrying member, the tensile-carrying member being selectively attached to the translational connection.

14. The device of claim 13 wherein the movement generator further comprises:
    a winch, the winch supplying a force to the tensile-carrying member to drag the device across the associated first frictional surface.

15. A portable device for measuring friction between a sample material and a road surface, the device comprising:
    a frame, the frame generally having the form of an equilateral triangle with first second and third points, the frame having first, second and third contacting regions located at the first, second and third points of the equilateral triangle, respectively;
    first, second and third sample holders, the first, second and third sample holders being located at an underside surface of the first, second and third contacting regions, respectively, the first, second, and third sample holders selectively holding associated first, second and third samples, respectively; the first, second and third associated samples each having an associated second frictional surface, wherein the height of one or more of the first, second, and third sample holders is adjustable;
    a translational connection, the translational connection being located the first point of the frame of the device;
    a movement generator, the movement generator selectively translating the device relative to the associated first frictional surface;
    a tensile carrying member, the tensile-carrying member being selectively attached to the translational connection;
    a motor, the motor supplying a force to the tensile-carrying member to drag the device across the associated road surface at a controllable speed; and,
    a force transducer, whereby the friction between the associated road surface and the samples may be measured.

16. The device of claim 15 wherein the heights of the first, second and third sample holders are independently adjustable from each other.

17. A method of measuring the frictional force resisting movement of an associated sample across an associated first frictional surface, the method comprising the steps of:
    mounting a sample in a sample holder attached to an underside of a portable friction testing device having a triangular configuration with three sample holders holding samples against the associated first frictional surface, wherein the height of one or more of the three sample holders is adjustable;
    translating the device across the associated first frictional surface, thereby moving the associated sample across the associated first frictional surface; and,
    measuring the frictional force generated by the translation.

18. The method of claim 17 where one sample is mounted in each of three sample holders, each of the sample holders being mounted on an underside of the device and at points of the device configured in an equilateral triangle.

19. The method of claim 17 wherein the heights of the three sample holders are independently adjustable from each other.

20. A device for measuring friction, the device comprising:
    a frame, the frame having first, second and third contacting regions, the first, second and third contacting regions capable of contacting an associated first frictional surface;
    a first sample holder, the first sample holder located near the first contact region, the first sample holder capable of securing an associated first sample in a position to contact the associated first frictional surface;
    a second sample holder, the second sample holder located near the second contact region, the second sample holder capable of securing an associated second sample in a position to contact the associated first frictional surface; and a third sample holder, the third sample holder located near the third contact region, the third sample holder capable of securing an associated third sample in a position to contact the associated first frictional surface;

wherein the second sample holder is adjustable between the second contact region and the first contact region, and wherein the third sample holder is adjustable between the third contact region and the first contact region.

* * * * *